United States Patent
Walker

[11] Patent Number: 6,106,673
[45] Date of Patent: Aug. 22, 2000

[54] METHOD FOR SEPARATING COMPONENTS OF A FERMENTATION PROCESS BYPRODUCT CONTAINING OIL BOUND WITH FIBERS

[75] Inventor: David Ray Walker, Clearwater, Fla.

[73] Assignee: CDC Environmental Corp., Tampa, Fla.

[21] Appl. No.: 09/004,469

[22] Filed: Jan. 8, 1998

[51] Int. Cl.[7] .............................. B01D 1/26; B01D 3/06; C02F 1/06; C02F 1/16

[52] U.S. Cl. ........................... 203/22; 159/17.1; 159/46; 159/47.3; 159/DIG. 8; 159/2.1; 203/27; 203/49; 203/71; 203/88; 426/472; 426/520; 435/276; 435/277; 210/770; 210/774

[58] Field of Search .................................. 159/2.1, 17.1, 159/47.3, DIG. 8, 47.1, 46; 34/427; 202/173, 174, 176; 210/767, 770, 774; 203/22, 25, 27, 71, 88, 49, DIG. 8; 426/520, 465, 472; 435/962, 276, 277, 272, 162, 182, 262.5, 173.9

[56] References Cited

U.S. PATENT DOCUMENTS

| | | | |
|---|---|---|---|
| 2,561,072 | 7/1951 | Reich | 435/164 |
| 3,993,535 | 11/1976 | Karnofsky | 159/47.1 |
| 4,503,079 | 3/1985 | King et al. | 426/494 |
| 4,952,504 | 8/1990 | Pavilon | 435/163 |
| 5,052,313 | 10/1991 | Walker | 110/346 |
| 5,080,581 | 1/1992 | Walker | 432/105 |
| 5,656,490 | 8/1997 | Wyatt et al. | 435/281 |
| 5,690,987 | 11/1997 | Parker et al. | 426/632 |

*Primary Examiner*—Virginia Manoharan
*Attorney, Agent, or Firm*—Boyle Fredrickson Ziolkowski S.C.

[57] ABSTRACT

A process and system are provided for the separation of a fermentation process byproduct into its constituent components and for the subsequent recovery of those constituent components. The process is remarkably simple—requiring only 1) heating of a mixture containing the byproduct so as to separate the oil from a base component of the byproduct to which the oil is bound, followed by 2) recovering the base product, oil, and possibly other substances such as molasses from the mixture. The process can be performed on a large scale and in a continuous fashion using a mechanical separator to recover fibers from a heated mixture to produce a solids stream and a liquor stream and by then removing oil and insoluble substances from the liquor stream in an evaporator assembly. Energy consumption and water consumption are minimized through 1) the use of waste heat from the system's dryer as an energy source for the evaporator assembly and 2) the use of condensed liquids from the evaporator assembly to dilute the mixture. Fibers recovered during the process can be dried efficiently in a way that produces a superior product.

29 Claims, 9 Drawing Sheets

METHOD FOR SEPARATING COMPONENTS OF A FERMENTATION PROCESS BYPRODUCT CONTAINING OIL BOUND WITH FIBERS

BACKGROUND OF THE INVENTION

1. Field of the Invention

The invention relates to fermentation byproduct treatment processes and systems and, more particularly, relates to an apparatus and system for separating a fermentation process byproduct into the byproduct's constituent components and for recovering those components.

2. Discussion of the Related Art

Fermentation processes are used in a wide range of industries to produce a variety of products. In the typical fermentation process, a starter or feed product is transformed into other substances in the presence of heat and/or a biological agent to produce a desired product as well as a byproduct. Feed or starter products for typical fermentation processes include fibrous organic materials such as grain meal or protein meal. The desired product of the fermentation process may, for instance, comprise an antibiotic. The byproduct of the fermentation process usually comprises a significant portion of the process' products.

The typical fermentation process byproduct is mixed in a liquid (usually water) and includes 1) insoluble solids, 2) dissolved soluble solids (primarily unconverted sugars), and 3) organic oils and fats. The insoluble solids usually comprise fibers and hence will usually be referred to herein as "fibers" for the sake of convenience. The oils and fats usually include one or more oils and one or more fats and will usually be referred to as "oil" herein for the sake of convenience. The oil usually binds to the fibers during the fermentation process so that it cannot be readily removed from the fibers by mechanical separation. This binding causes several problems, some of which will now be detailed.

The first problem arising from the binding of oil to the fibers of fermentation byproducts is that fiber drying is hindered. Fibers from fermentation process byproducts have a variety of potential applications including as fertilizer and as animal feed supplements. Fiber drying is desirable if not essential for shipment, storage, and/or post-processing of fibers used in most of these applications. However, drying of oil-saturated fibers by conventional methods is very difficult. If drying occurs at temperatures that are high-enough to separate the oil from the fibers by oxidation, the oil is destroyed, and the fiber may be damaged, thereby decreasing the digestibility of proteins in the recovered fibers and rendering the recovered fibers unsuited or at least poorly-suited for use as animal feed supplements or other, related applications. If, however, drying occurs at lower temperatures such that the oil separates from the fibers without oxidation, the oil coagulates on dryer components, reducing drying efficiency and creating fire risks. Some previous attempts to dry oil-bound fibers attempted to alleviate at least some of the problems associated with fiber drying by recycling a substantial percentage of dried products to the dryer inlet so that the resulting blended product that was subject to drying had a lower average oil content than an unblended product. These processes proved inefficient at best, and in most instances, proved infeasible.

A second problem associated with drying oil-bound fibers is that, even if the fibers can be adequately dried, the oil content of the resultant protein meal is too high for many uses. For instance, the fibers of the typical fermentation process byproduct are potentially highly useful as an animal feed supplement. However, because it was heretofore impossible to efficiently remove oils from the fibers during the drying processes, the dried product exhibited a substandard protein/oil ratio for use as a stand-alone feed supplement. That is, for most feed applications, if this product were fed to an animal in sufficient quantities to supply the animal with enough protein to thrive, the animal would consume too much oil with digestive problems. Hence, it was heretofore necessary to blend dried fermentation byproducts with other protein-based feeds to produce a blended feed with an acceptably high protein/oil ratio.

Another problem historically associated with handling fermentation process byproducts (as well as other products containing malodorous substances and/or bacterial contaminants) is that they are, at best, inefficient at sterilizing the byproducts or at destroying or at least rendering inert malodorous substances. Therefore, health and order concerns have placed additional constraints on companies' ability to handle fermentation byproducts and other, similar products.

As a result of the above-mentioned and other problems associated with separating oils from fibers of fermentation byproducts and with drying the oil-laden byproducts, the potential to put these byproducts into commercial use has never been fully realized. In fact, most manufacturers consider fermentation byproducts useful only as landfill materials and therefore must pay for the disposal of the byproducts, often at a cost of up to several million dollars per year and also must deal with potential health problems. Hence, many manufacturers of byproducts that have high concentrations of commercially valuable proteins, sugars, and oils must pay to dispose of these byproducts. The need therefore has arisen to provide a commercially-practical process and system that enable the recovery of valuable components and their associated revenue streams from a fermentation byproduct rather than having to deal with the disposal problems usually associated with the fermentation byproduct.

OBJECTS AND SUMMARY OF THE INVENTION

A first principal object of the invention therefore is to provide a process for recovering the individual components of a fermentation process byproduct so as to permit the recovered components to be dried and/or put to commercial use.

Another object of the invention is to provide a method that meets the first principal object and that can be performed on a commercial scale.

Another object of the invention is to provide a process that meets the first principal object of the invention and that can be performed on a large scale and in a continuous process.

In accordance with a first aspect of the invention, this object is achieved by providing a process comprising providing a mixture of the byproduct in a liquid, heating the mixture to separate the oil from the base component, and removing the oil from the mixture. The base component typically comprises a fiber, and the method preferably additionally comprises 1) removing the fiber from the mixture, 2) removing molasses from the diluted mixture, and 3) drying the fiber after the oil has been removed from the mixture.

In order to enhance uniform heating and to promote oil separation without reabsorption, the starting mixture, which typically contains less than 50% by weight of the byproduct, is diluted with a liquid, preferably water.

The heating step should take place at temperatures above the product's fermentation temperature but below a temperature at which proteins in the product begin to break down. The mixture preferably is heated to between about 140° F. and about 250° F., and even more preferably to about 200° F. The time for which the mixture must be held at this temperature, though product-dependent, varies generally inversely with temperature. A retention period of three minutes is preferred for a mixture heated to about 200° F.

The removing step preferably comprises removing the oil from the mixture by flash-evaporating a portion of the liquid to produce a high-velocity vapor which entrains at least a portion of the oil, and stripping the oil from the vapor. This removal preferably takes place in a primary evaporator supplemented, if necessary, by additional removal in a finishing evaporator.

Another object of the invention is to provide a process that meets at least the first principal object of the invention and that is efficient both from the standpoint of energy consumption and from the standpoint of water consumption.

In accordance with another aspect of the invention, this object is achieved by employing as the primary evaporator a waste heat evaporator receiving its heat energy from a dryer of the system and by recycling condensate from the evaporator(s) to a mixing tank of the system.

Another object of the invention is to provide a process that may meet the first principal object and that sterilizes contaminated products.

Still another object of the invention is to provide a process that may meet the first principal object and that reduces odors from the products.

A second principal object of the invention is to provide a system that is capable of recovering valuable components of a fermentation process byproduct.

Another object of the invention is to provide a system that meets the second principal object and that can operate on a commercial scale.

In accordance with another aspect of the invention, this object is achieved by providing a system that includes 1) a heater which is configured to heat a mixture of the byproduct in a liquid to a temperature which is sufficiently high to separate the oil from the base component, and 2) means for removing the oil from the mixture.

In order to assure that the product is sufficiently diluted for uniform heating and efficient oil separation, the system preferably additionally includes a mixing tank configured to mix a starting mixture containing less than 50% by weight of the byproduct with liquid so as to produce a diluted mixture.

A separator, located downstream of the heating tank and upstream of the means for removing, preferably is included in the system to remove insoluble solids from the diluted mixture. The separator may, for instance, comprises one of a centrifugal separator, a cyclonic separator, and a vacuum filter.

The means for removing could conceivably comprise a centrifuge, a ceramic filter, or the like, but preferably comprises an evaporator which removes at least a portion of the oil from the diluted mixture by flash-evaporating a portion of the liquid to produce a high-velocity vapor which entrains at least a portion of the oil.

Still another object of the invention is to provide a system that meets the second principal object of the invention and that is capable of recycling water and/or scavenging energy that would otherwise be wasted.

In accordance with another aspect of the invention, this object is achieved by providing a system which meets the second principal object and an evaporator of which receives its heat energy in the form of waste heat scavenged from a dryer of the system. In addition, dilution water for the mixing tank is obtained by recycling condensate from the evaporator.

Other objects, features, and advantages of the present invention will become apparent to those skilled in the art from the following detailed description and the accompanying drawings. It should be understood, however, that the detailed description and specific examples, while indicating preferred embodiments of the present invention, are given by way of illustration and not of limitation. Many changes and modifications may be made within the scope of the present invention without departing from the spirit thereof, and the invention includes all such modifications.

BRIEF DESCRIPTION OF THE DRAWINGS

A preferred exemplary embodiment of the invention is illustrated in the accompanying drawings in which like reference numerals represent like parts throughout, and in which.

DETAILED DESCRIPTION OF THE PREFERRED EMBODIMENTS

1. Resume

Figure 1:
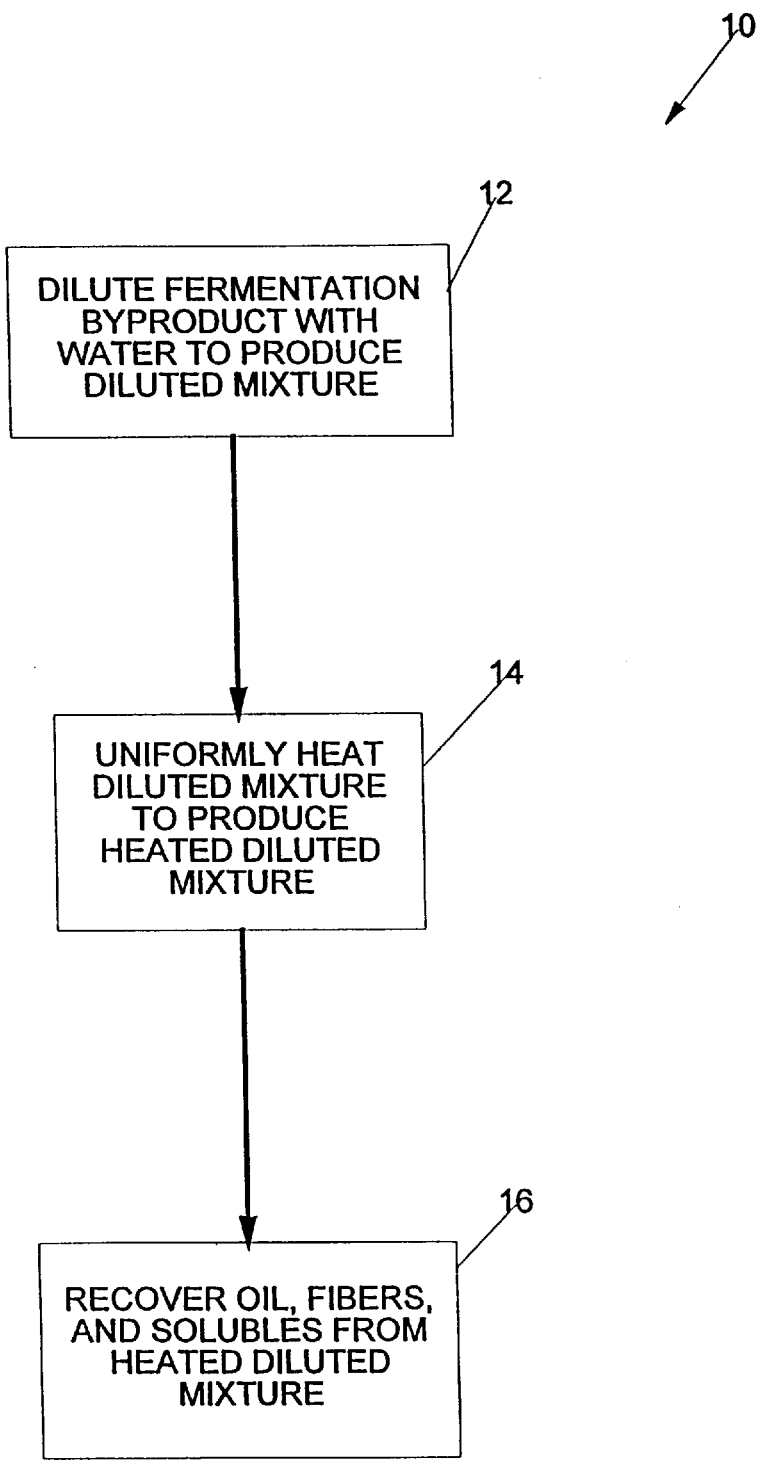
FIG. 1 is a simplified flow chart of a fermentation byproduct component separation and recovery process performed in accordance with the present invention.

Pursuant to the invention, a process and system are disclosed for the separation of a fermentation process byproduct into its constituent components and for the subsequent recovery of those constituent components. The process is remarkably simple—requiring only 1) heating of a mixture containing the byproduct so as to separate the oil from a base component of the byproduct to which the oil is bound, followed by 2) recovering the base product, oil, and possibly other substances such as molasses from the mixture. The process can be performed on a large scale and in a continuous fashion using a mechanical separator to recover fibers from a heated mixture to produce a solids stream and a liquor stream and by then removing oil and insoluble substances from the liquor stream in an evaporator assembly. Energy consumption and water consumption are minimized through 1) the use of waste heat from the system's dryer as an energy source for the evaporator assembly and 2) the use of condensed liquids from the evaporator assembly to dilute the mixture. Fibers recovered during the process can be dried efficiently in a way that produces a superior product.

2. Process Overview

The separation of a fermentation byproduct into its constituent components can be best understood by first understanding the composition of this byproduct and the manner in which it is produced. During the typical fermentation process, a mixture of a feed or starter product such as a grain meal or a protein meal in a liquid is heated to a fermentation temperature in the presence of a biological agent such as yeast. The fermentation process yields a desired product such as an antibiotic which can be recovered from the product in a known manner that, per se, forms no part of the present invention. After the desired product's recovery, a byproduct remains that is mixed with liquid and that typically includes three constituent components, namely 1) a base component, which typically (but not necessarily) comprises a fibrous substance that is high in protein and that will hereafter be referred to as "fibers" for the sake of convenience; 2) organic oils that typically comprises at least one and usually several different fats and oils and that hereinafter will be referred to as "oil" for the sake of convenience; and 3) soluble substances, principally non-convertible sugars. The oil of this byproduct is bound to the fibers due to the low heat of the fermentation process which heats the oil sufficiently to accelerate oil absorption into the cellular fibers without volatilizing the oil.

The invention resides in the separation of the oil from the fibers of a byproduct stream without permitting reabsorption of the oil into the fibers and in the recovery of the separated oil, fibers, and soluble substances from the byproduct stream. Component separation is achieved in a remarkably simple and effective manner simply by heating a mixture, preferably a diluted mixture, of the byproduct in a liquid such as water to a sufficiently-high temperature and for a sufficient length of time to cause the oil to separate from the fibers. The fibers and oil, being separated in a diluted solution of hot liquid, then can be recovered separately without permitting oil reabsorption into the fibers.

More specifically, referring to FIG. 1, the base process 10 preferably begins in Step 12 in which a fermentation process byproduct, which has been partially-dewatered to a liquid content of less than 40% by weight during recovery of the antibiotic or other desired fermentation product, is diluted with a suitable liquid. This dilution achieves two important benefits. First, it promotes uniform heating of the mixture (uniform heating is itself important for reasons detailed below). Second, dilution inhibits reabsorption of oil into the fibers during the intervening period between the separation and recovery processes. Dilution to at least 12% byproduct by weight or less is believed necessary to effectively prevent reabsorption of separated oils into the fibers. Dilution to less than 1% byproduct by weight inhibits subsequent oil recovery because it requires excess energy and equipment for oil recovery by the flash evaporation process detailed in Sections 3 and 4 below. Hence, enough liquid should be added to the byproduct to produce a diluted mixture containing between about 1% and 12%, and preferably about 5%, by weight of solid byproduct materials.

The liquid added to the byproduct in Step 12 preferably comprises water because water is inexpensive, non-corrosive, non-toxic, and is well-suited for the flash evaporation oil recovery process described in Sections 3 and 4 below. The invention therefore will be described primarily in conjunction with dilution with water, it being understood that it is also applicable to dilution with other liquids.

Referring again to FIG. 1, Step 14 of the process involves 1) the uniform heating of the diluted mixture to a separating temperature and 2) the retention of the diluted mixture at the separating temperature for a sufficient length of time to drive at least the majority of the oil from the fibers. Heating to a separating temperature is necessary to separate the oil from the fibers to which it is bound, and uniform heating to that temperature helps assure maximum oil separation. The "separating" temperature is one which is in excess of the product's fermentation temperature but below a temperature at which the proteins of the fibers begin to "cook" or break down. Cooking of the proteinaceous fibers or protein-based fibers should be avoided because it decreases protein digestibility and renders the recovered fibers unsuited or at least poorly-suited for use as an animal feed supplement or other, related applications. In the typical case in which the feed or starter product has a fermentation temperature of about 135° F. and in which protein breakdown or "cooking" begins at approximately 225° F., the diluted mixture should be heated to a separation temperature of between 135° F. and 225° F., and more preferably to a temperature of about 200° F.

Although the time/temperature profile for oil separation differs from product-to-product, the period over which the diluted mixture must be retained at the separation temperature for adequate oil separation is generally inversely related to the temperature at which separation occurs. It has been found that heating the average diluted mixture to a temperature of about 200° F. for a period of about 3 minutes provides optimum results. At this time, virtually all of the oil has been separated from the fibers and therefore is poised for recovery.

Component recovery is illustrated schematically in Step 16 of FIG. 1. This recovery usually will entail multiple steps, performed in-line and on a continuous basis. The bulk of the fibers typically are recovered from the diluted mixture by mechanical separation to produce a separate liquor and solids streams. Oil could conceivably be recovered from this liquor stream by mechanical separation either simultaneously with or after fiber separation, but preferably is recovered from the liquor stream after fiber separation by flash evaporation. After oil and fibers are recovered from the heated diluted mixture, the remaining concentrate has a high sugar content and can be thought of as a molasses.

The process 10 therefore produces three commercially-valuable products, namely 1) a fiber with a high protein content, an acceptably low oil content (and hence an acceptably high protein/oil ratio), and a high digestibility, 2) a light oil product, and 3) a molasses. Each of these components can be used separately after suitable post-processing operations such as fiber drying or oil winterizing. Alternatively, the molasses could be mixed with the fibers prior to fiber drying to enhance the viability of the resulting product for animal feed or related applications.

3. Fermentation Byproduct Separation and Recovery Process and System

A preferred, commercially viable process and system for carrying out the base recovery process 10 described in Section 2 above now will be detailed.

Figure 2:
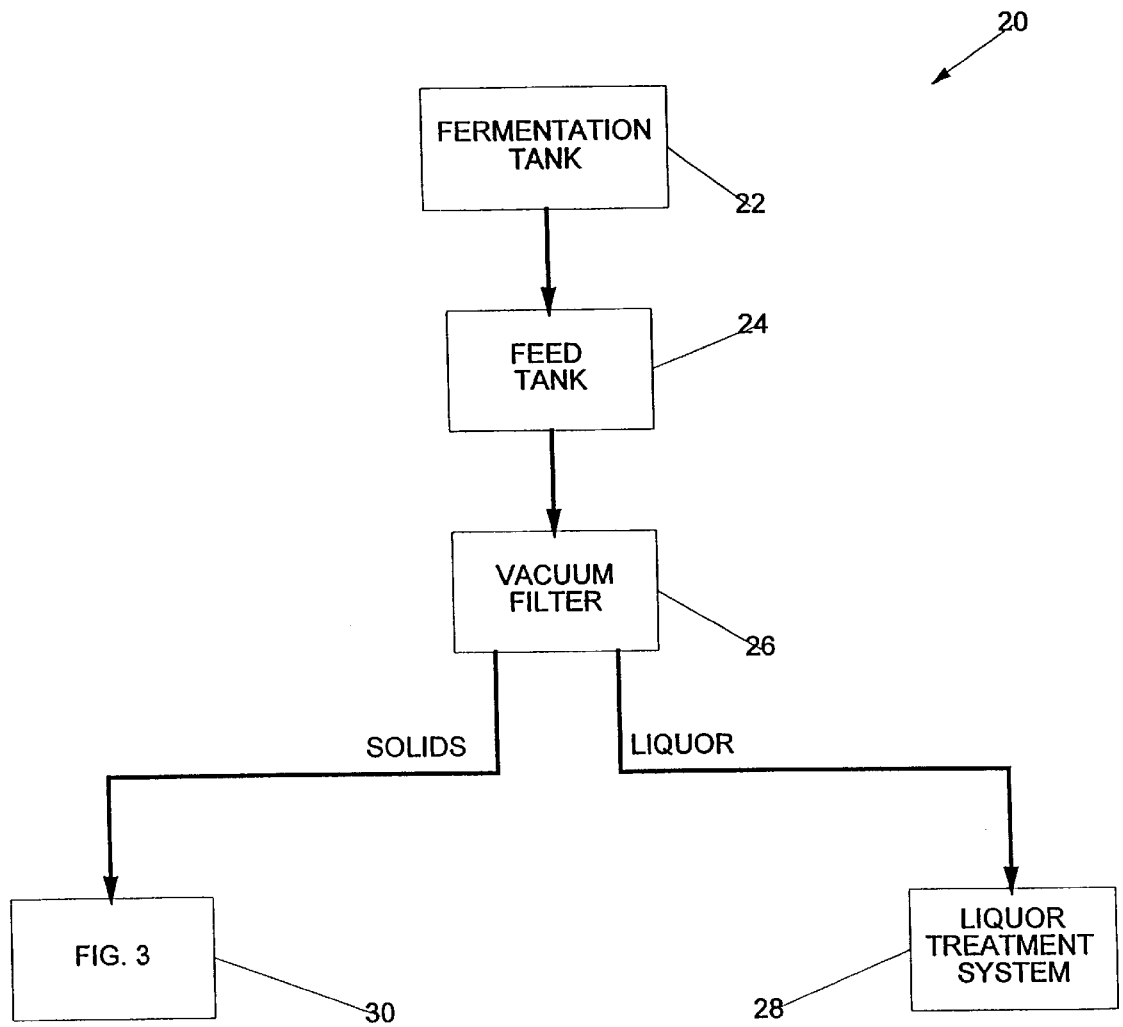
FIG. 2 schematically illustrates a fermentation system and a fermentation byproduct pre-treatment system usable in conjunction with the present invention.

Referring first to FIG. 2, a pre-processing system 20 is schematically illustrated for producing a fermentation byproduct with which the present invention is useful. The system 20 includes a conventional fermentation tank 22 in which a protein-based fibrous substance such as a grain meal or a protein meal undergoes fermentation by heating it in the presence of a biological substance such as yeast. After fermentation, the mixture includes the 1) a liquid such as water forming 82% to 95% of the mixture; 2) a desired fermentation product such as an antibiotic and 3) the fermentation byproduct described in Section 2 above and containing fibers, oil, and soluble substances.

This mixture is then fed from the fermentation tank 22 to a feed tank 24 in preparation for fermentation product recovery. The purpose of the feed tank 24 is to receive batches of products from the fermentation tank 22 and to feed the fermentation product to downstream recovery systems on a continuous basis. The feed tank 24 includes 1) internal agitators for maintaining the fermentation product therein thoroughly mixed and 2) a variable speed pump and/or a variable orifice valve for feeding the diluted fermentation product mixture to the downstream components of the system 20 at a constant, controlled rate.

The diluted mixture flowing from the feed tank 24 is dewatered, using the illustrated vacuum filter 26 or another suitable mechanical separator, to separate the mixture into two streams labeled "SOLIDS" and "LIQUOR", respectively in FIG. 2. The LIQUOR stream, which contains virtually all of the desired fermentation product and very little fermentation byproduct, is then conveyed to a liquor treatment system 28 in which the desired fermentation product is recovered from the liquor in a conventional manner which per se, forms no part of the present invention. The SOLIDS stream contains the fermentation byproduct mixed with water in a 1:3 ratio by weight. As discussed above, the byproduct in this stream includes oil-bound fibers and dissolved sugars and other soluble substances. The SOLIDS stream then is conveyed to a byproduct component separation and recovery system 30 constructed in accordance with the present invention.

Figure 3:
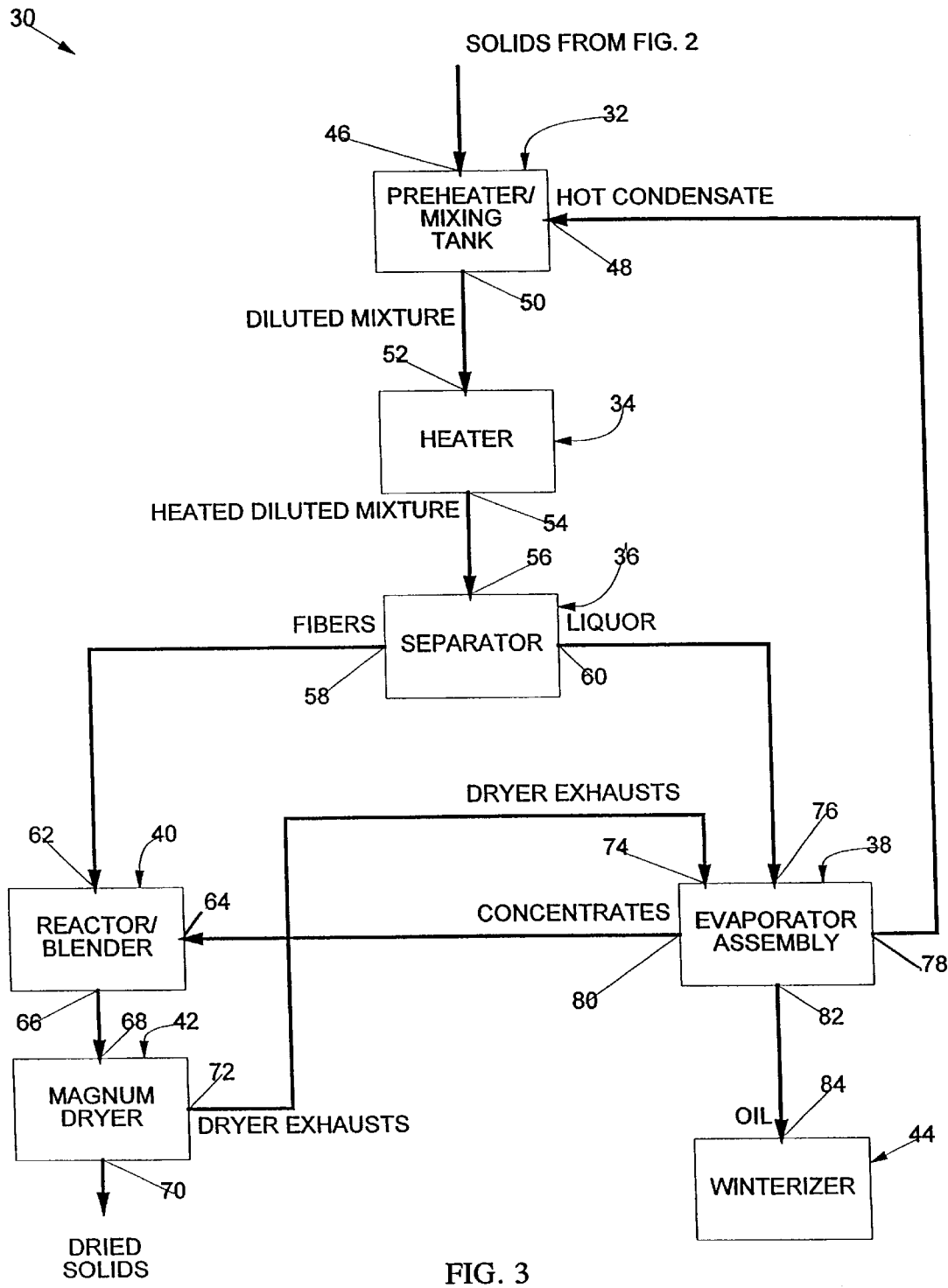
FIG. 3 schematically illustrates a fermentation byproduct component separation and recovery system constructed in accordance with the present invention.

Referring now to FIG. 3, the byproduct component separation and recovery system 30 includes as its principal components 1) a preheater/mixing tank 32 in which the aforementioned dilution Step 12 (FIG. 1) is performed; 2) a heater 34 in which the aforementioned heating Step 14 (FIG. 1) is performed, 3) a separator 36; and 4) an evaporator assembly 38. The aforementioned recovery Step 16 (FIG. 1) is performed by the separator 36 and the evaporator assembly 38, with the bulk of the fibers being recovered by the separator 36 and with the bulk of the oil and soluble substances being recovered by the evaporator assembly 38. The system 30 includes 1) a reactor/blender 40 for blending fibers and concentrates, recovered by the separator 36 and the evaporator assembly 38, to form a blended mix; 2) a dryer 42 for drying the blended mix; and 3) a winterizer 44 for separating oil into its constituent oil components.

The purpose of the preheater/mixing tank 32 is to dilute the dewatered fermentation product with water while simultaneously preheating the diluted mixture so as to reduce the energy requirements of the downstream heater 34. The preheater/mixing tank has 1) suitable inlets 46 and 48 for the dewatered byproduct stream and a source of hot liquid, preferably water, respectively (the inlets 46 and 48 could be composed as a single inlet receiving two different streams), and 2) a diluted mixture outlet 50. In order to reduce the energy and water requirements for the system 30, at least some of the water supplied to the inlet 48 preferably comprises condensate from the evaporator assembly 38. Disposed within the tank 32 is a suitable mixer such as a paddle wheel that thoroughly mixes the dewatered byproduct with the incoming hot water to assure uniform mixing and thorough preheating of the diluted mixture.

The purpose of the heater 34 is to heat the preheated diluted mixture discharged from the outlet 50 of the preheater/mixing tank 32 to the separation temperature described in Section 2 above (preferably about 200° F.) for a sufficient length of time to assure separation of the oil from the fibers (preferably about 3 minutes). As a result of this uniform heating, most of the oil will remain in the liquid phase during subsequent fiber/liquor separation in the separator 36 so that no more than about 10%, and preferably no more than about 5%, of the oil remains bound with the fibers. The separated fibers therefore are suitable for use as stand-alone feed supplements and other, related products. Hence, the product discharged from the heater 34 includes a mixture of water, fibers, separated oil, and dissolved soluble substances.

The heater 34 preferably comprises an in-line heater having an inlet 52 connected to the diluted mixture outlet 50 of the preheater/mixing tank 32 and an outlet 54 connected to an inlet 56 of the separator 36. The heater 34 may comprise any commercially-available heater capable of performing the desired functions. The heater 34 may, for instance, comprise a tank surrounded by an outer jacket containing steam or another heated fluid. The flow rate of the diluted mixture through the heater 34 is controlled so that the heated diluted mixture discharged from the outlet 54 has been heated to the desired separation temperature (about 200° F. in the preferred embodiment) for the desired separation time (about 3 minutes in the preferred embodiment) and hence to separate the oil from the fibers. The flow rate of diluted mixture through the heater 34 can be controlled, using feedback from temperature sensors located within the heater 34, through the modulation of a variable speed pump and/or through the modulation of a variable-orifice flow control valve located in series with the heater 34.

The purpose of the separator 36 is to separate the bulk of the fibers from a liquor stream containing water, oil, and dissolved soluble substances. The separator 36 can be thought of as a dewaterer because it separates the water and oil from the fibers. A variety of commercially-available devices could suffice for this purpose, so long as they operate with sufficient efficiency to separate at least most of the fibers from the liquid stream. The illustrated separator 36 has a diluted mixture inlet 56, a fibers outlet 58, and a liquid or liquor outlet 60. The separator 36 could, for instance, comprise a centrifuge, a cyclone separator, or a vacuum filter. In order to promote the use of the fibers as stand-alone supplements and other, related products, it is preferred that the separator 36 be configured to operate such that the fibers discharged from the solids outlet 58 include less than 10% by weight, and preferably less than 5% by weight, of oil. The remaining liquor stream discharged from outlet 60 typically will include about 96% water, 2% oil, and 2% soluble solids such as sugar.

Still referring to FIG. 3, the purpose of the reactor/blender 40 is to mix the fibers discharged from the separator 36 with concentrates discharge from the evaporator assembly 38 to produce a blended mixture suitable for drying in the dryer 42. The reactor/blender 40 would, of course, be eliminated if a separate use for the concentrates is contemplated. The illustrated reactor/blender 40 has first and second inlets 62 and 64 for the fibers and the concentrates, respectively (it being understood that the inlets 62 and 64 could be combined into a single integrated inlet), and an outlet 66 leading to an inlet 68 of the dryer 42. The reactor/blender 40 preferably comprises a paddle-type blender that thoroughly blends the fibers with the concentrates prior to discharging the blended mixture from the outlet 66. Depending upon the specific fermentation process, the agglomerative properties of the materials being processed, and the desired moisture level of the dried product exiting the dryer 42, a small percentage (typically about 10% to 30%) of dried solids may be recycled from the outlet 70 of the dryer 42 to one of the inlets 62 or 64 of the reactor/blender 40 in order to prevent the product from agglomerating or sticking on the paddles of the reactor/blender 40 or on internal components of the dryer 42 and to prevent burning or other drying problems. The recycle percentage also will depend on the product's optimal dryer input and output moisture contents.

The dryer 42 has 1) a wet product inlet 68 connected to the outlet 66 of the reactor/blender and 2) a dried solids outlet 70. The dryer 42 also has an exhaust gas outlet 72 that is coupled to an exhaust gas inlet 74 of the evaporator assembly 38 by suitable ductwork to permit scavenging of the waste heat from the dryer 42 and thereby to reduce the energy consumption of the system 30. Any of a variety of commercially-available dryers would be suitable for this purpose. It is preferred, however, that the dryer comprise a parallel flow, rotating drum dryer receiving heat energy from a burner (not shown). The dryer 42 also preferably includes a recycling conduit permitting the recycling of a desired percentage of relatively cool, recycled gases from the exhaust gas outlet 72 to the dryer inlet 68 to thereby ensure that mixing between the product and the gases occurs within the drying chamber 1) at a low-enough temperature to prevent product burning or charring and 2) at lower than ambient pressures. A particularly-preferred dryer, known as the "magnum dryer", is disclosed in U.S. Pat. No. 5,080,581 to Walker (the Walker '581 patent). The magnum dryer disclosed in the Walker '581 patent is a plate contact-type dryer operating at a low throat temperature and, when used in the present invention, dries the fiber product to a specified final moisture level (preferably about 10%) while maintaining high protein digestibility. The Walker '581 patent is hereby incorporated by reference in it entirety for its disclosure of a magnum dryer usable in the inventive system.

Still referring to FIG. 3, the evaporator assembly 38 may comprise any device or combination of devices capable of performing a flash evaporation or flash vaporization process that separates the oil from the liquid of the diluted mixture and that separates the liquid from the soluble solids, thereby producing separate streams of oil, clarified liquid condensate, and "concentrates" or a heavily-laden stream of sugars and/or other soluble solids. "Flash evaporation" is known in the art to involve the rapid evaporation or vaporization of at least a portion of a liquid stream to produce a high velocity vapor stream that entrains oils or other insoluble substances without actually oxidizing or vaporizing those substances. The typical flash evaporator assembly also includes internal scrubbers or other devices to condense the vapor stream and to separate the resultant condensate from the entrained substances.

The illustrated evaporator assembly 38 includes 1) a liquor inlet 76 connected to the liquor outlet 60 of the separator 36, 2) a hot condensate outlet 78 connected to the hot condensate inlet 48 of the preheater/mixing tank 32, 3) a concentrates outlet 80 connected to the concentrates inlet 64 of the reactor/blender 40, and 4) an oil outlet 82 connected to an oil inlet 84 of the winterizer 44. In the illustrated and preferred embodiment in which the evaporator assembly 38 receives at least part the energy for vaporization in the form of scavenged heat from the dryer 42, the evaporator assembly 38 also includes the above-mentioned exhaust inlet 74 which, as discussed above, is connected to the exhaust outlet 72 of the dryer 42. A particularly preferred evaporator assembly 38 is detailed in Section 4 below in conjunction with FIGS. 4–7.

The winterizer 44 separates the various constituent subproducts of the oil discharged from the oil outlet 82 of the evaporator assembly 38. Winterizer 44 is designed to retain the oil product stream from the evaporator assembly 38 at a sufficiently low temperature for a sufficient amount of time to separate wax and any remaining water from the oil so as to produce clarified light oil. Typically, the winterizer 44 will hold the oil at a temperature of about 35° F. for about 12 days. The winterizer is, per se, well known, and accordingly, will not be described in further detail.

The operation of the fermentation byproduct separation and recovery system 30 is believed to be self-evident from the description above but will be summarized for the sake of convenience.

A partially dewatered stream of fermentation byproduct, typically containing between 15% and 40% by weight of the byproduct and most typically about 25% by weight of the byproduct, is fed into the byproduct inlet 46 of the preheater/mixing tank 32 at a temperature of about 135° F. and at a flow rate of about 6,500 lbs/hr. Hot condensates and/or hot water from another source at a temperature of about 180° F. are also fed into the tank 32 via inlet 48 at a rate of about 10,500 lbs/hr and mixed with the dewatered byproduct to dilute the mixture to about 5% by weight of the fermentation byproduct and to preheat the diluted mixture to a temperature of about 175° F. The preheated diluted mixture then is discharged from the outlet 50 of the preheater/mixing tank 32 and conveyed to the heater 34 at a flow rate of 17,000 pounds per hour, where it is heated to a separation temperature of about 200° F. and retained at that temperature for about 3 minutes as it flows through the heater 34 to separate the oil from the fibers. The heated diluted mixture is then discharged from the outlet 54 of the heater 34 and fed to the inlet 56 of the separator 36. The separator 36 separates the bulk of the fibers from the diluted mixture to discharge a heavily solids-laden stream from the fibers outlet 58 and a liquor stream from the liquor outlet 60. The solids-laden stream is then fed to the inlet 62 of the reactor/blender 40 from the solids outlet 58 at a flow rate of 4,250 lbs/hr and mixed with concentrates from the evaporator assembly 38 arriving at the concentrates inlet 64 at a flow rate of 1,740 lbs/hr. The blended products, having an initial moisture content of 60% to 72% by weight, are then dried in the magnum dryer 42 to a moisture level of about 10%. As discussed above, some of the dried products can, if necessary, by recycled from the dryer outlet 70 to the reactor/blender inlet 40 to facilitate the blending and drying processes. It should be emphasized that, unlike prior attempts to dry fermentation byproducts without first separating the oil from the byproducts, dried solids recycling is not critical to the drying process and can be eliminated altogether for many products without serious detriment.

The liquor stream discharged from the liquor outlet 60 of the separator 36 is fed into the liquor inlet 76 of the evaporator assembly 38 at a flow rate of 12,750 lbs/hr and typically will contain 96% water, 2% oil, and 2% soluble solids such as sugar. The evaporator assembly 38 then separates this stream into its constituent components and discharges streams hot condensate, concentrates and oil from the outlets 78, 80, and 82 at typical flow rate of 10,500 lbs/hr, 1,740 lbs/hr, and 510 lbs/hr, respectively. The oils are then winterized in the winterizer 44.

Another advantage of the process described in this Section is that the byproducts are sterilized (i.e., bacteria and other potentially-harmful contaminates are destroyed or neutralized) without damaging the proteins, sugars, or oils. Sterilization occurs in the heater 34 where the byproduct is heated to temperature above which many bacteria can survive. Odor-producing VOC's are separated from the solids during the oil recovery process so that the dried and sterilized products are essentially odor-free.

4. Construction and Operation of Evaporator Assembly

Figure 4:
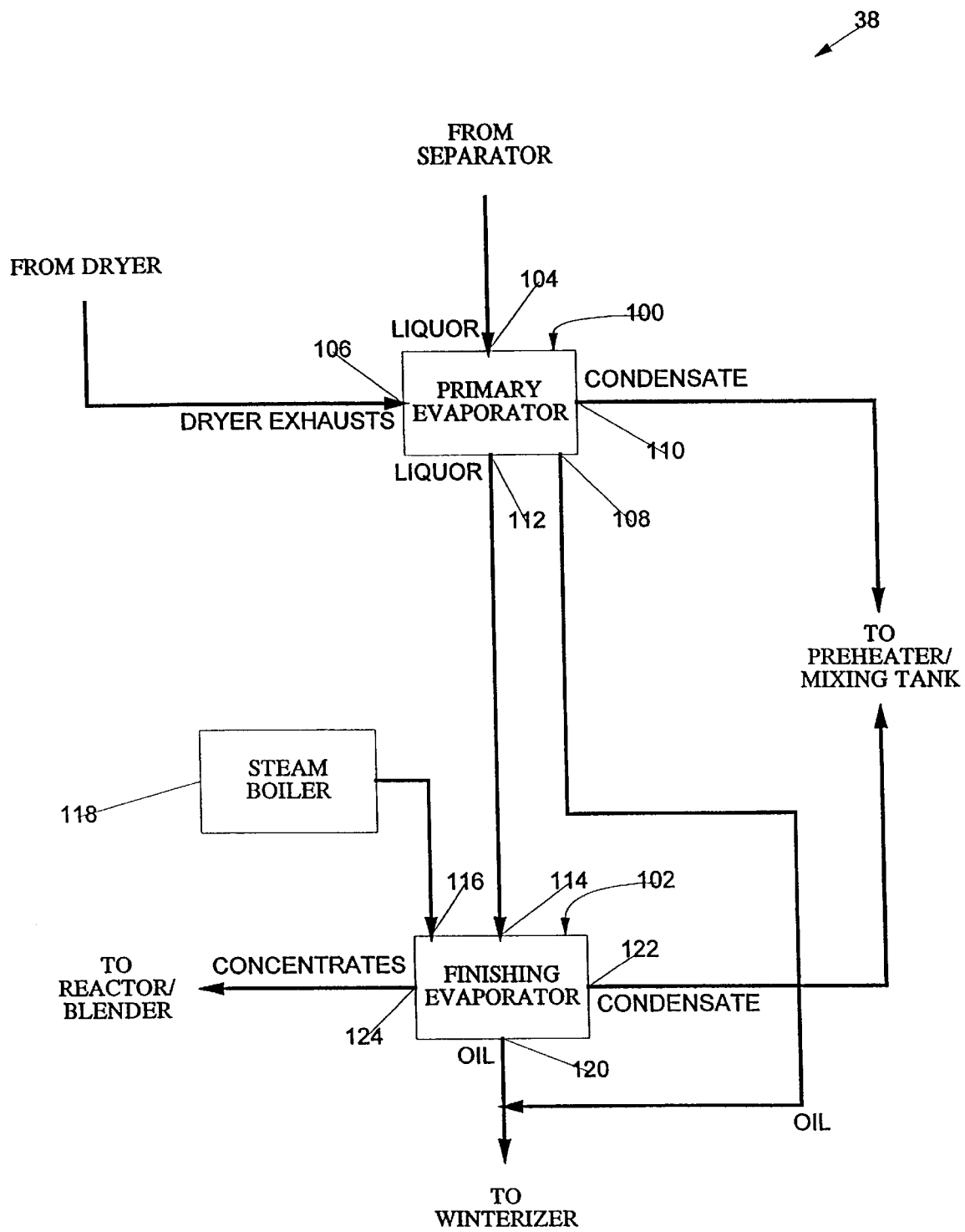
FIG. 4 schematically illustrates an evaporator assembly usable in the fermentation byproduct component separation and recovery system of FIG. 3.

Referring now to FIG. 4, the evaporator assembly 38 includes at least one, and possibly two or more evaporators each of which removes oil from the liquor stream discharged from the separator 36 by flash evaporation, i.e, by entrainment of the oil with high-velocity water vapor. Only a single evaporator would be necessary in most systems. The illustrated system includes both a primary evaporator 100 and a finishing evaporator 102 to accommodate a perceived worst-case scenario in which the liquor has a very high initial water content, in which a very high percentage of the oil must be removed from the liquor, and/or in which the oil is difficult to separate from the water. The primary evaporator 100 includes 1) a liquor inlet 104 connected to the primary liquor inlet 76 of the assembly 38; 2) an exhaust gas inlet 106 connected to the inlet 74 of the evaporator assembly 38; 3) an oil outlet 108 connected to the oil outlet 82 of the evaporator assembly 38; 4) a condensate outlet 110 connected to the condensate outlet 78 of the evaporator assembly; and 5) a liquor outlet 112 connected to a liquor inlet 114 of the finishing evaporator. The finishing evaporator 102 includes 1) the liquor inlet 114; 2) a steam inlet 116 which receives steam from a boiler 118; 3) an oil outlet 120 connected to the oil outlet 82 of the evaporator assembly 38; 4) a condensate outlet 122 connected to the condensate outlet 78 of the evaporator assembly 38; and 5) a concentrate outlet 124 connected to the concentrate outlet 80 of the evaporator assembly 38. The bulk of the oil and solubles are separated from the liquor in the primary evaporator 100, and the remaining separation occurs in the finishing evaporator 102.

Figure 5:
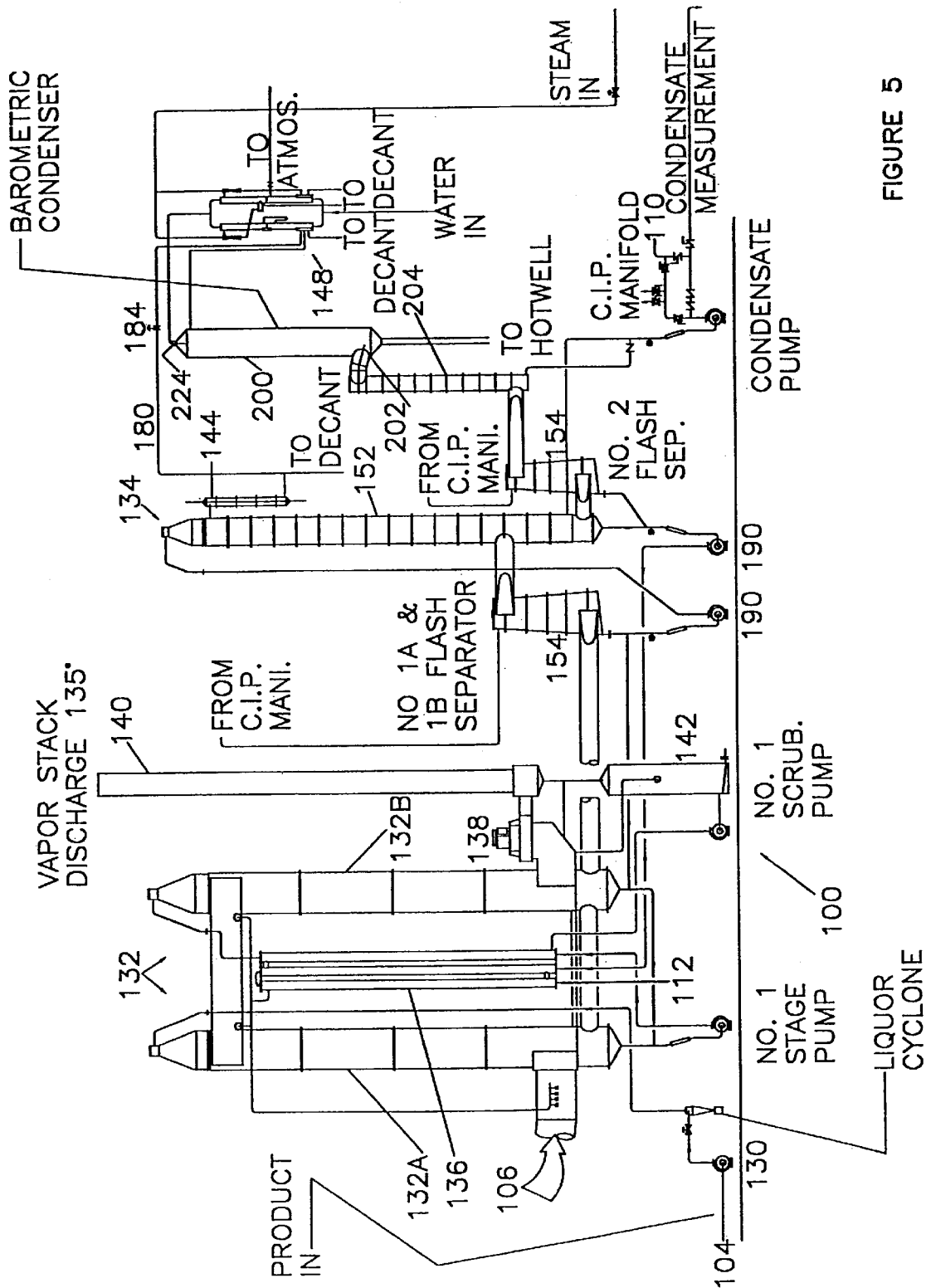
FIG. 5 is a partially schematic, sectional side view of a primary, waste heat evaporator of the evaporator assembly of FIG. 4.

Turning to FIG. 5, the primary evaporator 100 now will be described primarily by way of its operation. Primary evaporator 100 preferably but not necessarily comprises a waste heat evaporator receiving its heat energy from the dryer 42. It uses a feed pump 130 to introduce liquor from the liquor inlet 104 to a multiple effect evaporator which, in the illustrated embodiment, comprises a two-effect, three-stage system having a stripper system for oil recovery. The primary evaporator 100 can be generally described as a continuous, single pass, multiple-effect evaporator. Each "effect" is a unit describing the heat energy flow through the evaporator 100. The first effect receives heat from the primary heat source (the exhaust gas outlet 72 of the dryer 42 in the illustrated embodiment). Each subsequent use of heat from the first effect is assigned a numerically higher designation through the evaporator 100. Energy use always progresses from the highest temperature to the lowest temperature in the evaporator 100. Hence, a second effect 134 receives heat energy from the first effect 132, and any third and subsequent effects (not present in this embodiment) receive heat energy from the second effect 134. Each "effect" consists of at least one set of concentric shell-and-tube vessels (known as a "tubenest") that are designed to transfer energy from a saturated vapor stream to evaporate water in the tubes as the saturated vapor stream flows upwardly through the surrounding shell. The first effect 132 actually includes two tubenests 132A and 132B located on opposite sides of a shell-and-tube heat exchanger 136. The second effect 134 and any subsequent effects (not present in this embodiment) each include only a single tubenest. Air from various points in the evaporator assembly 100 is separated from oil and water vapor in an air removal system 148 before being discharged to the atmosphere.

The "stages" of the evaporator 100 describe the path of product flow. The first stage therefore is that portion of the evaporator 100 which receives the liquor stream from the separator 36, and each of the first and second effects 132 and 134 can be thought of as a separate stage. The illustrated evaporator 100 therefore comprises a two effect, three stage evaporator.

Exhaust flow through the evaporator 100 is controlled by a vapor induction fan 138 that is located at a discharge point of the first effect 132 and that vents the exhaust gases out of a stack 140. Condensate lost by this cooled vapor stream is collected in a scrubber tank 142. The scrubber tank 142 removes fine particles and maintains water therein at a temperature close to that of the condensed dryer vapor, typically about 180° F. The hot water in this tank 142 preheats the inbound liquor from the separator 36 in the heat exchanger 136.

The liquor then flows through the first and second effects 132 and 134 in sequence in indirect heat exchange with streams of hot gases or vapors. In each effect, the liquor becomes progressively more concentrated with sugar or other soluble substances due to the removal of oil-laden water vapor therefrom. As the liquor is concentrated, the evaporated vapor of the first effect 132 provides energy for vaporizing more water in the second effect 134.

Vapors are propelled from effect to effect by a progressive reduction in temperature and a resultant reduction in volume and hence a reduction of pressure as the vapor moves through the evaporator 100 from effect to effect. Oil-laden vapors are vented from the second effect 134, directed to a condenser 144 by a duct 180, and condensed and decanted from the water to produce the oil stream.

Each of the effects 132 and 134 operates similarly. The second effect 134 therefore will be detailed, it being understood that, operationally, the same description applies equally to the first effect 132. A liquor stream enters the second effect 134 from above and flows downwardly through the second effect, where a portion of the water therein undergoes flash evaporation. The vapor stream from the second effect 134 then is separated from liquid entrained therewith. A vapor stream from the first effect 132 flows upwardly into the second effect 134 from below, where the more volatile water condenses and the less volatile oil is vented.

Figure 6:
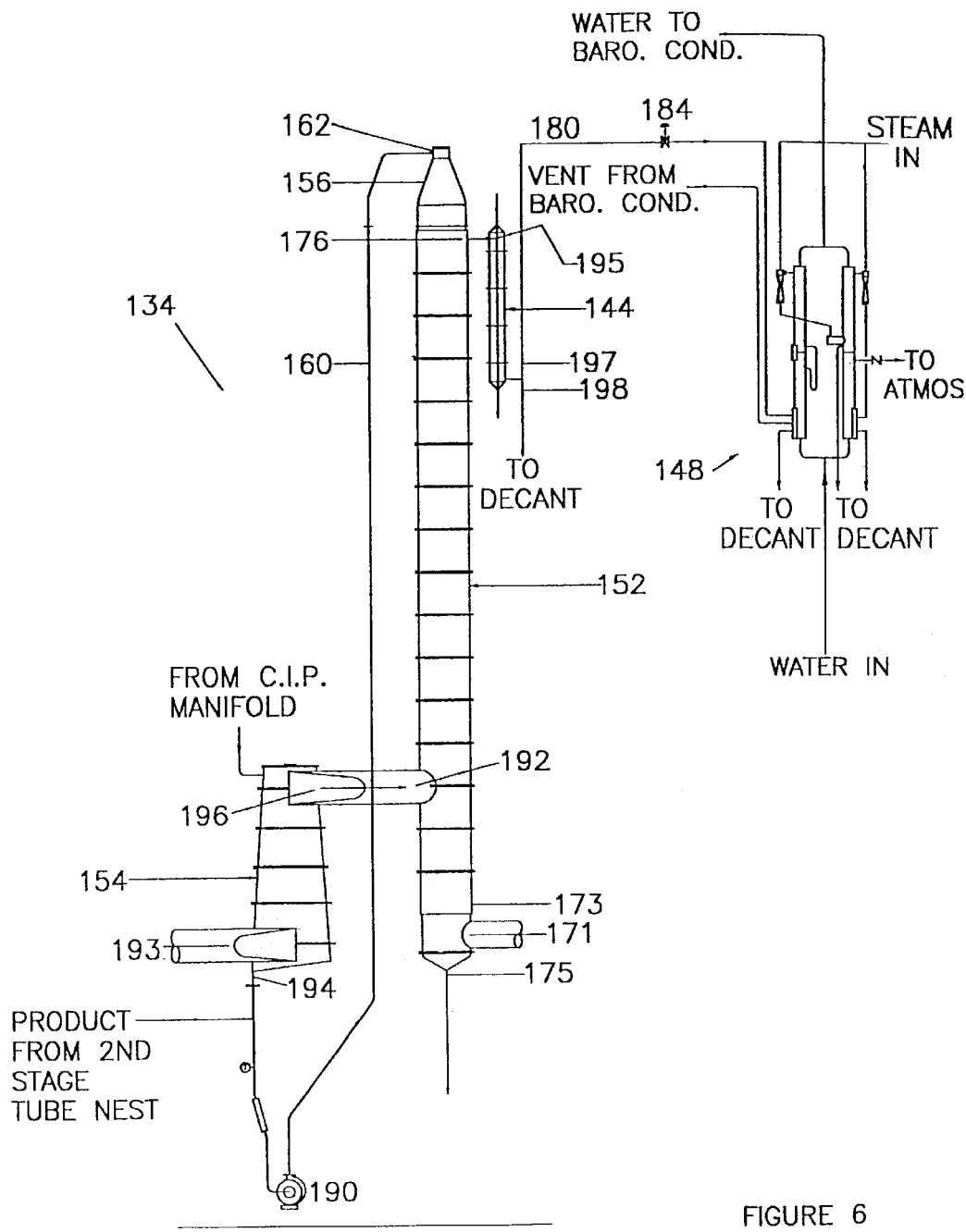
FIG. 6 is a partially schematic elevation view of one of the effects of the evaporator of FIG. 5.
Figure 7:
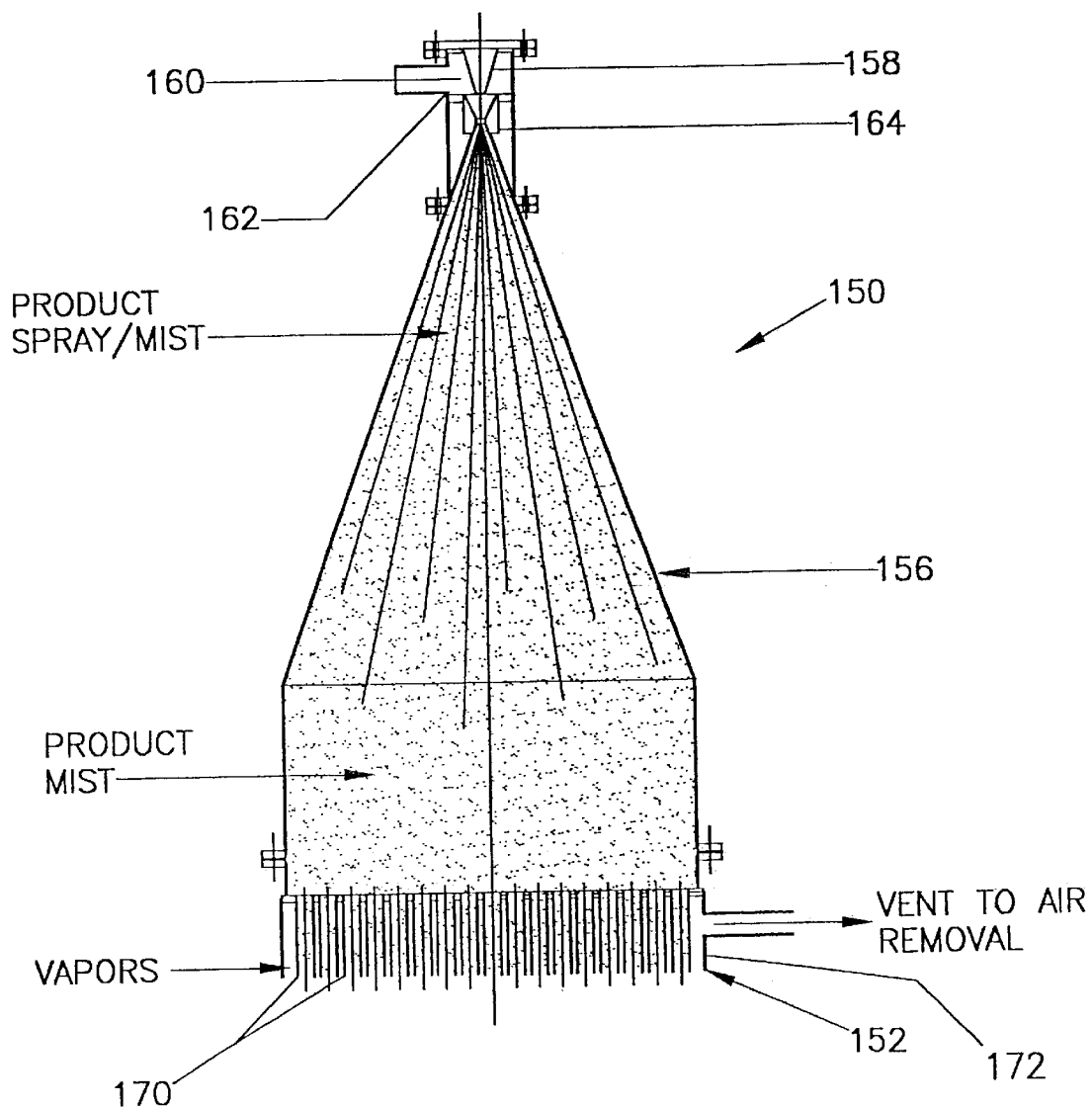
FIG. 7 is a sectional elevation view of a distribution section and a cooperating portion of the evaporator effect of FIG. 6.
Figure 8:
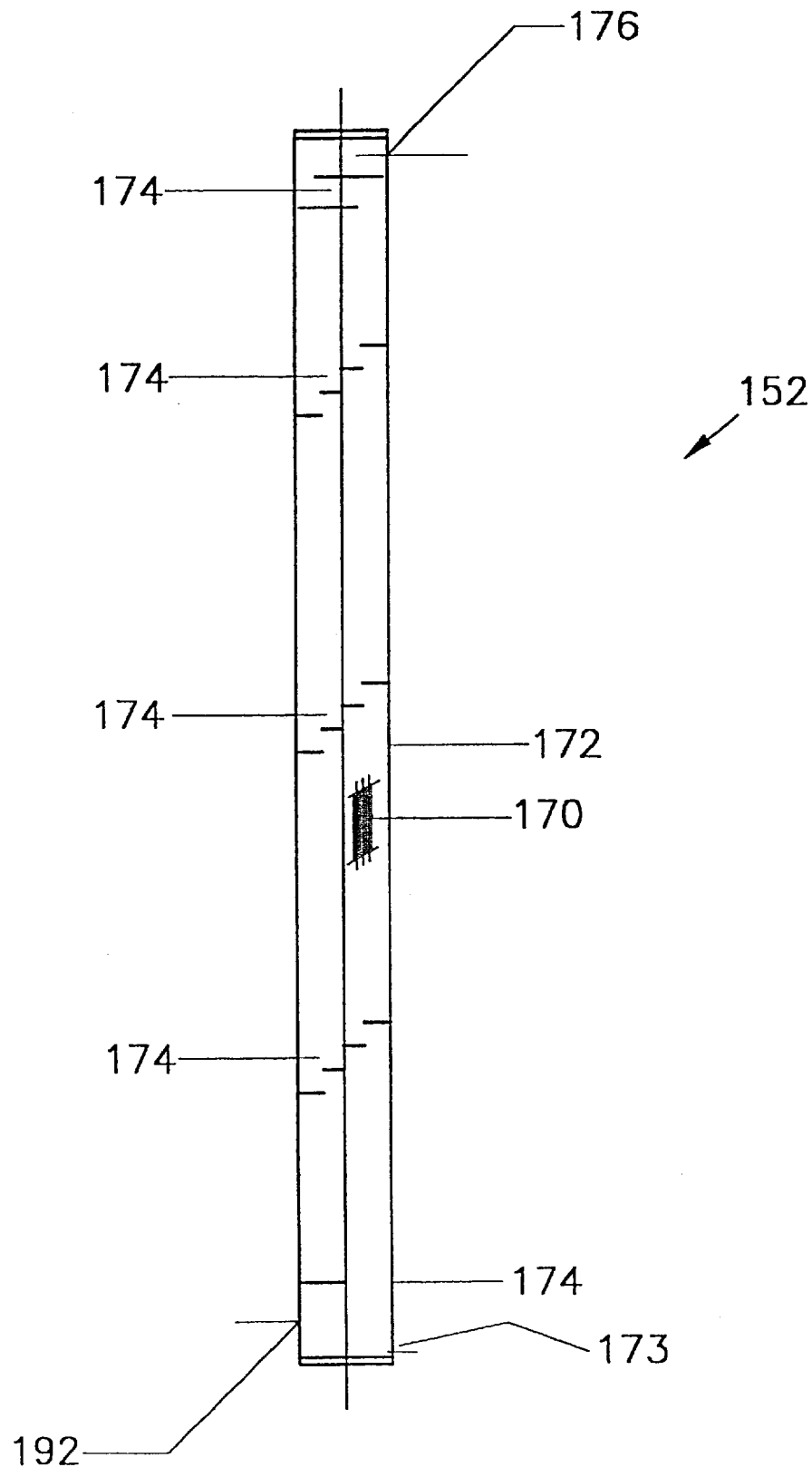
FIG. 8 is a sectional elevation view of a shell of the tubenest of FIG. 7.

Referring now to FIGS. 6–8, the second effect 134 consists of three interrelated parts, namely 1) a distribution section 150 and 2) a tube bundle or tubenest 152, and 3) a liquid/vapor separator 154.

The distribution section 150, best seen in FIG. 7, includes 1) a distribution cone 156 located above the tubenest 152 and 2) an expansion nozzle 158 located in a conduit 160 leading to a liquor inlet 162 located at the apex of the distribution cone 156. The nozzle 158 converts the liquid to a liquid-vapor mixture by flashing a small portion of the liquid into a vapor as it expands through the nozzle 158. The liquid-vapor is accelerated by the vapor expansion from the flash, and then is fed through the conduit 160 into a second nozzle 164 at the apex of the distribution cone 156, best seen in FIG. 7. A large pressure drop results from product flow through the nozzle 164, the area of which has a ratio to the area of the outlet of the distribution cone 156 of 1:200. This large pressure drop accelerates the product stream and causes rapid expansion. In fact, the liquid-vapor mix expands in the distribution cone 156 to approximately 60 times its original volume, thus atomizing the remaining liquid into a turbulent mist. This thermally exploding mist fills the entire distribution cone 156 as it flows downwardly through the cone 156.

The tubenest 152 comprises a shell-and-tube heat exchanger the tubes 170 of which receive mist from the distribution cone 156 from above and the shell 172 of which receive vapor from the preceding effect from below. The turbulent mist from the distribution cone 156 falls freely through the tubes 170 in the tubenest 152 and absorbs heat through the tube walls from the hot vapors rising upwardly trough the adjacent shell 172. Because the product falling through the tubes 170 is in the form of a fog or mist, the absorption of heat from the vapor in the shell 172 causes evaporation of about an additional 2% of the entrained water in the mist, which further increases the mist volume. The mist is thus thermally accelerated by continuous adsorption of heat and volumetric expansion of the mist through the entire length of the tubenest 152. Vapor velocity at a lower exit 171 of the tubenest can be has high as 170 feet/sec. This high-velocity vapor stream entrains a significant amount of oil with it. The remaining liquor drains out of an outlet 175 and is pumped back to the heat exchanger 136.

Referring again to FIGS. 5–8, Oil is stripped from the vapor by an oil stripper system having a first portion disposed within the shell 172 of the tubenest 152 of the second effect 134 and a second portion disposed remote from the second effect 134. The first portion is designed to take advantage of the fact that oil is less volatile than water and removes the oil and a small portion of the vapor stream from the remainder of the vapor stream. The second portion removes the remaining vapor from the oil by condensation.

The first portion of the oil stripper takes the form of a plurality of vertically-staggered, horizontally-extending baffling plates 174 that are disposed in the shell 172 of the tubenest 152 of the second effect 134 as seen in FIG. 8. The baffles 174 force the vapor to travel through the shell 172 in a generally serpentine path, without unacceptably decelerating the high-velocity vapor, as the vapor travels upwardly from a vapor inlet 192 to a vapor outlet 176. The entire vapor stream transfers heat to the mist in the tubes 170 at this time. Most of the relatively volatile water condenses and drains out of the shell 172 through a condensate outlet 173, leaving a vapor stream that is heavily-laden with oil at the upper end of the tubenest 152.

Referring again to FIGS. 5–7, each separator 154 may, for example, comprise a dry wall separator or a centrifugal vapor-liquid separator having an inlet 193 which receives the vapor stream leaving the bottom of tubenest of the first effect 132. The illustrated separator 154 uses the high-velocities of the vapor to divide the mixture into vapor and liquid components from the first effect 132 in a manner which is, per se well known. The concentrated liquid drains from an outlet 194 into the suction side of a pump 190 at the bottom of first effect 132 and then is pumped into the inlet 162 of the second effect 134. The vapor is discharged from an outlet 196 to the inlet 192 of the shell 172 of the tubenest 152.

The oil-laden vapor stream from the second effect 134 is vented from the outlet 176 of the tubenest 152 as seen in FIG. 5 by a duct assembly 180 under control of a vacuum controller 184 which may, for instance, comprise a simple manually operated valve. The exhausted oil-laden vapors are conveyed to the condenser 144 and air removal system 148, which, in combination, form the second portion of the oil stripper and remove the oil from the condensate to provide separate streams of oil and clarified condensate under power of a pressure differential thereacross. The condenser 144, which, per se, has a vapor inlet 195, a vapor outlet 197, and an oil outlet 198. A portion of the incoming water vapor is partially condensed in the condenser 144 by transferring heat to condensate discharged from the evaporator 100. The resulting liquid stream comprises oil, water, and small amounts other non-condensible substances. The oil is separated from the water by decanting and then is discharged from the outlet 108 of the evaporator 100 (FIG. 4) and conveyed to the winterizer 44 for further handling as described in Section 3 above.

Figure 9:
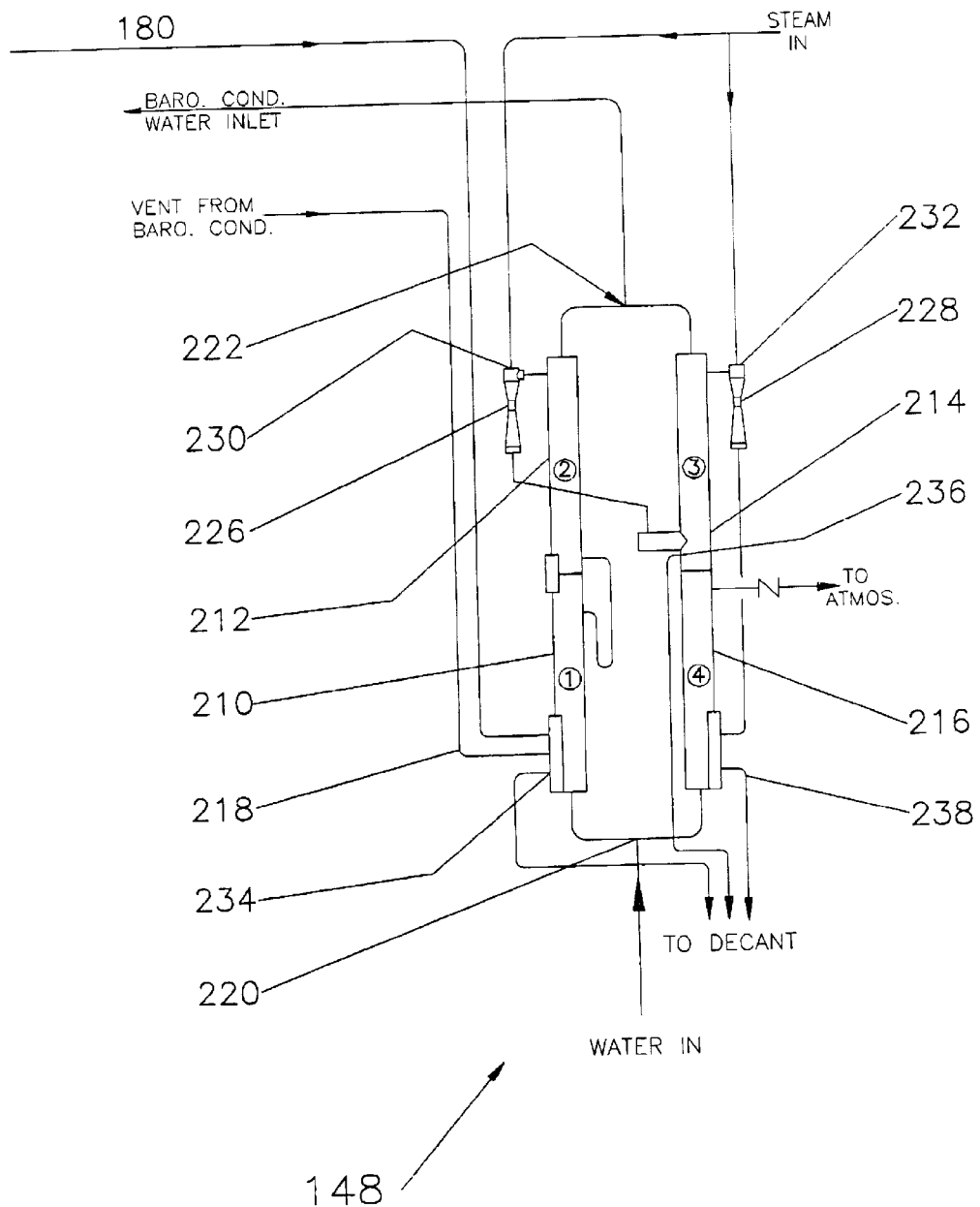
FIG. 9 is an elevation view of an air removal system of the evaporator of FIG. 5.

The remaining vapor from the condenser 144, which still entrains some oil, is discharged from vapor outlet 197 and ducted to the inlet 218 of the air removal system 148. The air removal system 148 is, per se, known. Referring especially to FIG. 9, the air removal system 148 includes four condenser stages 210, 212, 214, and 216 in which heat is transferred to the vapor stream (1) to condense the water from the vapor stream and (2) to remove the oil from the vapor stream by entrainment with the condensed vapor. The outside water flows into an inlet 220 of the air removal system 148, then receives heat from the vapor in the various condenser stages 210, 212, 214, and 216 to condense the water vapors, and then is discharged from a water outlet 222 of the air removal system 148 and conveyed to an inlet 224 of the barometric condenser 200 to condense vapors from second effect 134 as detailed below. Movement of vapor streams, oil streams, and water streams through the air removal system 148 is driven by steam in a pair of jets 226 and 228. The jets 226 and 228 receive steam from inlets 230 and 232 of the air removal system 148. First and second oil-laden streams are discharged from respective first, second, and outlets 234, 236, and 238 of the air clarifier system 148. The oil-laden stream from the outlet 234 is combined with the condensate stream from the condenser 144 and decanted before the resulting oil stream is discharged from the oil outlet 108 of the evaporator assembly 100. The oil-laden stream from the outlets 236 and 238 may also be combined with the stream from the outlet 234 or, alternatively, may be decanted separately to produce a separate oil stream that may be sold separately.

Referring again to FIG. 5, after the vapor stream is drawn through both effects 132 and 134 of the evaporator 100 and has essentially all of the oil stripped therefrom as described above, it is drawn into an inlet 202 of a condenser 200 by a conduit 204 and condensed by transferring heat to water flowing into the above-mentioned inlet 224 of the condenser 200. The condenser 200 may, for instance, comprise a barometric condenser or a surface condenser. Generally, a surface condenser will be used only if the final vapor condensate must remain separate from the cooling water. Vapor is drawn from a vapor outlet 206 of the condenser 200 and directed into the inlet 218 of the first condenser stage 210 of the air removal system 148, where water is condensed and oil is removed in the four condenser stages 210, 212, 214, and 26 as described above.

The product flowing from the outlet 173 of the second effect 134 comprises hot clarified condensate having a temperature of about 135° F. to 154° F. This product then is conveyed to the outlet 82 of the evaporator assembly 38 and then to the inlet 48 of the preheater/mixing tank 32 as described above.

If the primary evaporator 100 is the only evaporator in the evaporator assembly 38, the concentrate stream discharged from the outlet 110 will be essentially free of oil and hence will not require further separation. If further separation is required, the primary concentrate will be a liquor that serves as an input for the finishing evaporator 102. Returning again to FIG. 4, the finishing evaporator 102 comprises a so-called thermally accelerated short time evaporator (T.A.S.T.E.) that differs from the waste heat evaporator 100 primarily in that the first stage is modified to use steam from the boiler 118 as a heat source rather than scavenged he at from the dryer 42. Since the T.A.S.T.E. finishing evaporator 102 does not vary conceptually from the waste-heat primary evaporator 100 described above (apart from lacking scrubbers and other equipment which clarify dryer exhaust gases and which would not be necessary in a system utilizing steam as a heat source) and, in any event, does not, per se, form part of the present invention, the finishing evaporator 102 will not be detailed. Those interested in the details of its design can obtain those details from CDC Environmental Corp., Tampa, Fla.

In summary, the inventive fermentation process byproduct separation and recovery process and system produce high-quality, commercially valuable products from a byproduct that often otherwise would have to be land-filled or otherwise disposed of. These products include a dried fiber with a high protein/oil ratio and a high digestibility, a light fat/oil product, and molasses which can be dried or used as a feed dressing. The process can be performed on a large-scale, continuous manner. The process also is energy efficient and conserves minimal make-up water.

Many changes and modifications could be made to the process and the system as described without departing from the spirit thereof. For instance, the process is not necessarily limited to the recovery of substances from a fermentation process byproduct, but could instead additionally apply to the other processes in which oil is bound to a base component of a product. Moreover, as discussed above, the evaporator assembly need not include two evaporators as described. It is also conceivable that the evaporator assembly could be replaced by a ceramic filter, a centrifuge or some other device capable of removing oil from water after the oil has been separated from the water. In addition, fiber drying is not essential to the basic process. Even if a dryer is present in the system, the molasses could be dried separately or put to some other use rather than being blended with the fibers prior to drying. Nor is the base component of the fermentation process byproduct subject to the invention necessarily limited to fibers, nor are the oils that are bound to the base component limited to "oil" as that term is defined above. The scope of other changes will become apparent from the appended claims.

I claim:

1. A process of separating an oil of a fermentation process byproduct from a base component of said byproduct to which said oil is bound, said process comprising:
    (A) mixing a starting mixture of said byproduct with a liquid to form a diluted mixture of said fermentation process byproduct and said liquid;
    (B) uniformly heating said diluted mixture to a temperature of between about 135° F. and about 225° F. to separate said oil from said base component; and then
    (C) removing said oil from said diluted mixture.

2. A process as defined in claim 1, wherein said base component comprises a fiber, and further comprising 1) removing said fiber from said diluted mixture and 2) removing a molasses from said diluted mixture.

3. A process as defined in claim 2, further comprising drying said fiber after said oil has been removed from said diluted mixture.

4. A process as defined in claim 1, wherein the starting mixture contains said liquid and less than 50% by weight of said byproduct.

5. A process as defined in claim 4, wherein said starting mixture contains between 15% and 40% by weight of said byproduct.

6. A process as defined in claim 4, wherein said starting mixture contains about 25% by weight of said byproduct.

7. A process as defined in claim 1, wherein said diluted mixture contains between about 1% and 12% by weight of said byproduct.

8. A process as defined in claim 7, wherein said diluted mixture further contains about 5% by weight of solid product materials.

9. A process as defined in claim 1, wherein, following the heating step, said diluted mixture comprises said liquid, insoluble solids, said oil, and soluble substances dissolved in said liquid, and wherein the removing step comprises removing said oil from said diluted mixture by 1) flash-evaporating a portion of said liquid to produce a vapor which entrains at least a portion of said oil, and 2) stripping said oil from said vapor.

10. A process as defined in claim 9, further comprising removing an insoluble solids-laden stream from said diluted mixture by a process selected from the group consisting of centrifugal separation, cyclonic separation, and vacuum filtration.

11. A process as defined in claim 9, wherein
    at least a portion of the removing step is performed in a plurality of successive stages in a multiple-effect evaporator, and wherein, in each stage, heat is transferred to a liquid portion of said diluted mixture so as to produce 1) a vapor stream that entrains a portion of said oil, and 2) a concentrated liquid stream that contains any remaining oil and said soluble substances, and wherein, in each of the second and subsequent stages, heat is transferred to said liquid portion of said diluted mixture from the immediately-preceding stage.

12. A process as defined in claim 11, wherein said evaporator is a waste heat evaporator, and wherein heat is supplied to a first stage of said evaporator as waste heat scavenged from a step selected from the group consisting of said mixing step, said heating step, and said removing step.

13. A process as defined in claim 1, wherein said liquid comprises water.

14. A process as defined in claim 1, further comprising drying said base component in a dryer.

15. A process as defined in claim 1, wherein the heating step comprises uniformly heating said mixture to a temperature of about 200° F. and continues for about three minutes.

16. A process of separating an oil of a fermentation process byproduct from a base component of said byproduct to which said oil is bound, said process comprising:
    (A) mixing a starting mixture of said byproduct with a liquid to form a diluted mixture of said fermentation process byproduct and said liquid;
    (B) heating said diluted mixture to separate said oil from said base component; and then
    (C) removing said oil from said diluted mixture, wherein the heating step comprises uniformly heating said diluted mixture to a temperature of between about 140° F. and about 250° F.

17. A process as defined in claim 16, wherein the heating step comprises uniformly heating said diluted mixture to a temperature of about 200° F. and continues for about three minutes.

18. A process of separating an oil of a byproduct from a base component of said byproduct to which said oil is bound, said process comprising:

(A) mixing said byproduct with a liquid to form a diluted mixture;

(B) heating said diluted mixture to separate said oil from said base component; and (C) removing said oil from said diluted mixture, wherein, following the heating step, said diluted mixture comprises said liquid, insoluble solids, said oil, and soluble substances dissolved in said liquid, and wherein the removing step comprises removing said oil from said diluted mixture by 1) flash-evaporating a portion of said liquid to produce a vapor which entrains at least a portion of said oil, and 2) stripping said oil from said vapor, wherein at least a portion of the removing step is performed in a plurality of successive states in a multiple-effect evaporator, and wherein, in each stage, heat is transferred to a liquid portion of said diluted mixture so as to produce 1) a vapor stream that entrains a portion of said oil, and 2) a concentrated liquid stream that contains any remaining oil and said soluble substances, and wherein, in each of the second and subsequent stages, heat is transferred to a liquid portion of said diluted mixture from the immediately-preceding stage, wherein said evaporator is a waste heat evaporator, and wherein heat is supplied to a first stage of said evaporator as waste heat scavenged from a step selected from the group consisting of said mixing step, said heating step, and said removing step, and further comprising drying at least said insoluble solids in a dryer, and wherein heat is supplied to said first stage of said evaporator from said dryer.

19. A process of separating an oil of a byproduct from a base component of said byproduct to which said oil is bound, said process comprising:

(A) mixing said byproduct with a liquid to form a diluted mixture;

(B) heating said diluted mixture to separate said oil from said base component; and (C) removing said oil from said diluted mixture, wherein, following the heating step, said diluted mixture comprises said liquid, insoluble solids, said oil, and soluble substances dissolved in said liquid, and wherein the removing step comprises removing said oil from said diluted mixture by 1) flash-evaporating a portion of said liquid to produce a vapor which entrains at least a portion of said oil, and 2) stripping said oil from said vapor, wherein at least a portion of the removing step is performed in an evaporator, and wherein, said evaporator comprises a primary evaporator, and wherein another portion of said removing step is performed in a plurality of successive stages in a multiple-effect finishing evaporator located downstream of said primary evaporator, and wherein, in each stage of said finishing evaporator, heat is transferred to a liquid portion of said diluted mixture so as to produce 1) a vapor stream that entrains at least another portion of said oil, and 2) a concentrated liquid stream that contains any remaining oil and said soluble substances, and wherein, in each of the second and subsequent stages of said finishing evaporator, the heat is transferred to the liquid portion of the diluted mixture from the immediately-preceding stage.

20. A process of separating an oil of a byproduct from a base component of said byproduct to which said oil is bound, said process comprising:

(A) mixing said byproduct with a liquid to form a diluted mixture;

(B) heating said diluted mixture to separate said oil from said base component; and (C) removing said oil from said diluted mixture, wherein, following the heating step, said diluted mixture comprises said liquid, insoluble solids, said oil, and soluble substances dissolved in said liquid, and wherein the removing step comprises removing said oil from said diluted mixture by 1) flash-evaporating a portion of said liquid to produce a vapor which entrains at least a portion of said oil, and 2) stripping said oil from said vapor, wherein said evaporator comprises a primary evaporator, and wherein another portion of said removing step is performed in a plurality of successive stages in a multiple-effect finishing evaporator located downstream of said primary evaporator, and wherein, in each stage of said finishing evaporator, heat is transferred to a liquid portion of said diluted mixture so as to produce 1) a vapor stream that entrains at least another portion of said oil, and 2) a concentrated liquid stream that contains any remaining oil and said soluble substances, and wherein, in each of the second and subsequent stages of said finishing evaporator the heat is transferred to the liquid portion of the diluted mixture from the immediately-preceding stage, wherein said finishing evaporator receives heat energy from an external heat source.

21. A process of separating an oil of a byproduct from a base component of said byproduct to which said oil is bound, said process comprising:

(A) mixing said byproduct with a liquid to form a diluted mixture;

(B) heating said diluted mixture to separate said oil from said base component; and (C) removing said oil from said diluted mixture, wherein, following the heating step, said diluted mixture comprises said liquid, insoluble solids, said oil, and soluble substances dissolved in said liquid, and wherein the removing step comprises removing said oil from said mixture by 1) flash-evaporating a portion of said liquid in an evaporator to produce a vapor which entrains at least a portion of said oil, and 2) stripping said oil from said vapor, and wherein the mixing step comprises mixing condensate from said evaporator with said byproduct to produce said diluted mixture and to preheat said byproduct.

22. A process of separating an oil of a byproduct from a base component of said byproduct to which said oil is bound, said process comprising:

(A) mixing said byproduct with a liquid to form a diluted mixture;

(B) heating said diluted mixture to separate said oil from said base component; and (C) removing said oil from said diluted mixture, wherein, following the heating step, said diluted mixture comprises said liquid, insoluble solids, said oil, and soluble substances dissolved in said liquid, and wherein the removing step comprises removing said oil from said diluted mixture by 1) flash-evaporating a portion of said liquid to produce a vapor which entrains at least a portion of said oil, and 2) stripping said oil from said vapor, and wherein a soluble substance-laden liquid concentrate remains after said removing step, and further comprising 1) removing said insoluble solids from said diluted mixture prior to said removing step and 2) drying said insoluble solids and said liquid concentrate in a dryer.

23. A process of separating an oil of a fermentation process byproduct from a base component of said byproduct to which said oil is bound, said process comprising:

(A) mixing a starting mixture of said byproduct with a liquid to form a diluted mixture of said fermentation process byproduct and said liquid;

(B) heating said diluted mixture to separate said oil from said base component; then (C) removing said oil from said diluted mixture; and (D) sterilizing said base component during said heating step.

24. A process of separating an oil of a fermentation process byproduct from a base component of said byproduct to which said oil is bound, said process comprising:

(A) mixing a starting mixture of said byproduct with a liquid to form a diluted mixture of said fermentation process byproduct and said liquid;

(B) heating said diluted mixture to separate said oil from said base component; then (C) removing said oil from said diluted mixture; and (D) stripping malodorous VOC's from said byproduct during the step of removing said oil from said diluted mixture.

25. A process of separating an oil of a fermentation process byproduct from fibers of said byproduct to which said oil is bound, said process comprising:

(A) mixing said byproduct with a liquid to produce a diluted mixture of said byproduct and said liquid, said diluted mixture containing less than 12% by weight of said byproduct;

(B) uniformly heating the diluted mixture to a temperature of between 135° F. and 250° F. for a sufficient period of time to separate said oil from said fibers;

(C) removing said fibers from said diluted mixture, and (D) removing said oil from said diluted mixture by
(1) flash-evaporating a portion of said liquid to produce a vapor which entrains at least a portion of said oil, and then
(2) stripping said oil from said vapor.

26. A process of separating an oil of a fermentation process byproduct from fibers of the byproduct to which said oil is bound, said process comprising:

(A) mixing a starting mixture containing less than 50% by weight of said byproduct with a clarified condensate to produce a diluted mixture containing less than 12% by weight of said byproduct; then (B) uniformly heating the diluted mixture to a temperature of between 135° F. and 250° F. for a sufficient period of time to separate said oil from said fibers;

(C) removing said fibers from said diluted mixture by a process selected from the group consisting of centrifugal separation, cyclonic separation, and vacuum filtration;

(D) drying said fibers; and (E) removing said oil from said diluted mixture by
(1) flash-evaporating water from said diluted mixture so as to produce a) a residual concentrated liquid stream containing at least some soluble substances and b) a stream of vapor which entrains at least some of said oil, and then
(2) stripping said oil from said vapor and condensing said vapor to produce said clarified condensate and oil.

27. A process of separating an oil of a fermentation process byproduct from fibers of the byproduct to which said oil is bound, said process comprising:

(A) mixing a starting mixture containing less than 50% by weight of said byproduct with a clarified water condensate to produce a diluted mixture containing less than 12% by weight of said byproduct; then (B) uniformly heating the diluted mixture to a temperature of between 135° F. and 250° F. for a sufficient period of time to separate said oil from said fibers, thereby sterilizing said byproduct and dividing said diluted mixture into water, said fibers, said oil, and soluble substances dissolved in water; then (C) removing said fibers from said diluted mixture by a process selected from the group consisting of centrifugal separation, cyclonic separation, and vacuum filtration;

(D) drying said fibers; and (E) removing said oil and malodorous VOCs from said diluted mixture by
(1) flash-evaporating a portion of said water so as to produce a) a molasses and b) a stream of vapor which entrains at least some of said oil,
(2) stripping said oil from said vapor and condensing said vapor to produce a stream of said clarified water condensate and a stream of said oil, wherein
at least a portion of said evaporating step is performed in a plurality of successive stages in a single pass, multiple-effect evaporator, and wherein,
in each stage, heat is transferred to a liquid portion of said diluted mixture so as to produce 1) said vapor stream that entrains at least a portion of said oil, and 2) a concentrated liquid stream that contains any remaining oil and said soluble substances, and wherein, in each of the second and subsequent stages, heat is transferred to the liquid portion of the mixture from the immediately-preceding stage.

28. A process of separating an oil of a fermentation process byproduct from a base component of said byproduct to which said oil is bound, said process comprising:

(A) mixing a mixture of said byproduct with a liquid to form a diluted mixture of said fermentation process byproduct and said liquid; then (B) uniformly heating the diluted mixture to a temperature of between 135° F. and 225° F. for a sufficient period of time to separate said oil from said fibers; and then (C) removing said fibers from said diluted mixture and removing said oil from said diluted mixture.

29. A process of separating an oil of a product from a base component of said product to which said oil is bound, said process comprising:

(A) mixing a starting mixture, containing less than 50% by weight of said byproduct, with a liquid condensate to form a diluted mixture having a temperature of between 110° F. and 180° F.;

(B) adding a liquid to said diluted mixture;

(C) heating said diluted mixture to separate said oil from said base component; and then (D) removing said oil from said diluted mixture, wherein, following the heating step, said diluted mixture comprises said liquid, insoluble solids, said oil, and soluble substances dissolved in said liquid, and wherein the removing step comprises removing said oil from said diluted mixture by 1) flash-evaporating a portion of said liquid to produce a vapor which entrains at least a portion of said oil, and 2) stripping said oil from said vapor.

* * * * *